United States Patent
Abi-Kheirs

(10) Patent No.: US 9,370,370 B2
(45) Date of Patent: Jun. 21, 2016

(54) SHAPE MEMORY HEMOSTASIS BAND

(75) Inventor: Michael Abi-Kheirs, Natick, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1084 days.

(21) Appl. No.: 11/284,735

(22) Filed: Nov. 22, 2005

(65) Prior Publication Data

US 2007/0118162 A1    May 24, 2007

(51) Int. Cl.
*A61B 17/08* (2006.01)
*A61B 17/122* (2006.01)
*A61B 17/00* (2006.01)
*A61F 2/30* (2006.01)

(52) U.S. Cl.
CPC ... *A61B 17/1227* (2013.01); *A61B 2017/00867* (2013.01); *A61F 2002/30092* (2013.01); *A61F 2210/0014* (2013.01)

(58) Field of Classification Search
CPC ............... A61B 2017/00867; A61B 17/1227; A61F 2002/30092; A61F 2210/0014
USPC ......... 623/23.72; 606/142, 143, 157, 48, 151, 606/140
See application file for complete search history.

(56) References Cited

U.S. PATENT DOCUMENTS

| | | | | |
|---|---|---|---|---|
| 4,414,721 A * | 11/1983 | Hufnagel | ...................... | 606/142 |
| 4,556,050 A * | 12/1985 | Hodgson et al. | ................. | 600/30 |
| 5,356,416 A * | 10/1994 | Chu et al. | ...................... | 606/140 |
| 5,398,844 A * | 3/1995 | Zaslavsky et al. | ............ | 221/208 |
| 5,697,940 A * | 12/1997 | Chu et al. | ...................... | 606/140 |
| 5,968,056 A * | 10/1999 | Chu et al. | ...................... | 606/140 |
| 5,972,001 A * | 10/1999 | Yoon | .............................. | 606/139 |
| RE36,629 E * | 3/2000 | Zaslavsky et al. | ............ | 221/208 |
| 6,042,591 A * | 3/2000 | Mears | ........................... | 606/140 |
| 6,059,797 A * | 5/2000 | Mears | ........................... | 606/140 |
| 6,059,798 A * | 5/2000 | Tolkoff | ........................ | 606/140 |
| 6,136,009 A * | 10/2000 | Mears | ........................... | 606/140 |
| 6,162,238 A | 12/2000 | Kaplan et al. | | |
| 6,280,452 B1 * | 8/2001 | Mears | ........................... | 606/140 |
| 6,325,809 B1 * | 12/2001 | Bryars | ......................... | 606/139 |
| 6,436,108 B1 * | 8/2002 | Mears | ........................... | 606/140 |

(Continued)

FOREIGN PATENT DOCUMENTS

| | | |
|---|---|---|
| EP | 1 238 638 | 9/2002 |
| WO | 98/58591 | 12/1998 |
| WO | 02/39906 | 5/2002 |

OTHER PUBLICATIONS

Maekawa S et al., Endoscopic Variceal Scleroligation Therapy with a Newly Designed Multiple-Band Ligator Device with Special Groove, New Groove-Type Band Ligator, Endoscopy 2004; 36: 378.*

(Continued)

*Primary Examiner* — Corrine McDermott
*Assistant Examiner* — Sarah Simpson
(74) *Attorney, Agent, or Firm* — Fay Kaplun & Marcin, LLP

(57) ABSTRACT

A tissue constriction device comprises a tissue-surrounding part defining a central, tissue-receiving opening which, when in a tissue-receiving configuration, has a first diameter and which, when in a tissue-constriction configuration, has a second diameter less than the first diameter, at least a shape memory portion of the tissue-surrounding part being formed of a shape memory material with the tissue-constriction configuration corresponding to a memorized shape of the shape memory portion.

21 Claims, 2 Drawing Sheets

(56) References Cited

U.S. PATENT DOCUMENTS

| | | | |
|---|---|---|---|
| 6,607,542 B1 * | 8/2003 | Wild | 606/157 |
| 6,685,713 B1 * | 2/2004 | Ahmed | 606/140 |
| 7,025,776 B1 * | 4/2006 | Houser et al. | 606/213 |
| 2005/0080454 A1 | 4/2005 | Drews et al. | |
| 2005/0191248 A1 * | 9/2005 | Hunter et al. | 424/50 |
| 2005/0251201 A1 * | 11/2005 | Roue et al. | 606/213 |
| 2006/0259041 A1 * | 11/2006 | Hoffman et al. | 606/139 |
| 2007/0191884 A1 * | 8/2007 | Eskridge et al. | 606/213 |

OTHER PUBLICATIONS

Communication Pursuant to Article 94(3) EPC (from related European Application No. 06 817 069.5), dated Jan. 21, 2010.

* cited by examiner

SHAPE MEMORY HEMOSTASIS BAND

BACKGROUND

Internal bleeding resulting from, for example, the progress of a disease or as a complication following surgery, may have serious health consequences. This bleeding may take place deep inside the body, for example, in the gastrointestinal tract ("GI tract"). Invasive surgery may be required to control such bleeding exposing the patient to the risks associated with such procedures. Thus, less invasive alternatives have been sought. For example, endoscopic procedures have been employed to treat bleeding within the GI tract and within various other body lumens. As would be understood by those skilled in the art, an endoscope is basically a hollow tube which is placed at a desired location within the body to facilitate access to target tissue via either a natural body orifice or a relatively small incision. The endoscope itself does not often carry out the required procedures, but is fitted with a lumen, or internal channel, permitting a user to insert medical devices therethrough and to control these devices from the proximal end of the endoscope using controls which remain outside the body.

Internal bleeding is often treated via hemostasis (i.e., stopping blood flow within a vessel by mechanically constricting the vessel). A common hemostasis technique involves the use of an elastic band, similar to a small rubber band, which is deployed via a deployment device adapted to fit on an endoscope around a portion of a blood vessel to prevent blood from flowing therethrough. In many applications, the band, which is formed of an elastic material, is applied to the blood vessel while stretched and, after being positioned around the vessel, is released to constrict to a reduced diameter to clamp the vessel and cause hemostasis. The person operating the device uses the endoscope to manipulate the deployment device and to position it at the desired location based, for example, on feedback from vision tools of the endoscope. The operator may also use the vision tools to evaluate the outcome of the procedure.

SUMMARY OF THE INVENTION

In one aspect, the present invention is directed to a tissue constriction device comprising a tissue-surrounding part defining a central, tissue-receiving opening which, when in a tissue-receiving configuration, has a first diameter and which, when in a tissue-constriction configuration, has a second diameter less than the first diameter. At least a shape memory portion of the tissue-surrounding part is formed of a shape memory material with the tissue-constriction configuration corresponding to a memorized shape of the shape memory portion.

In another aspect, the present invention is directed to a method for treating fluid leakage within a living body, comprising inserting into the body a first tissue-constricting element formed of a shape memory material with the first tissue-constricting element in a first tissue-receiving configuration, a tissue-entry opening of the first tissue-constricting element having a diameter which, when in the tissue-receiving configuration, is greater than when the first tissue-constricting element is in a tissue-constricting configuration and drawing a first portion of tissue into the tissue-entry opening while maintaining the first tissue-constricting element in the tissue-receiving configuration in combination with causing the first tissue-constricting element to move to the tissue-constricting configuration to strangulate the first portion of tissue.

DETAILED DESCRIPTION

Figure 2:
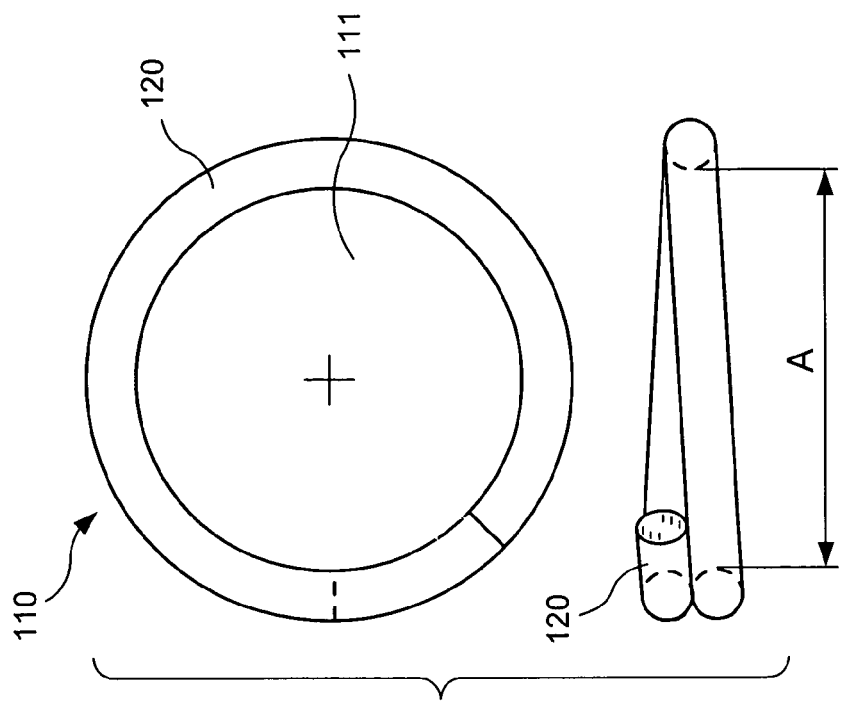
FIG. 2 is a diagram showing an embodiment of a shape memory hemostasis band in an expanded condition according to the invention.

The present invention may be further understood with reference to the following description and the appended drawings, wherein like elements are referred to with the same reference numerals. The present invention is related to medical devices used to treat internal bleeding in a patient. More specifically, the present invention is related to devices which cause hemostasis by constricting the flow of blood through a blood vessel. The blood vessel may be located within the GI tract of the patient, and may be difficult to reach using conventional methods. Those skilled in the art will understand that, although the invention is described in regard to hemostasis, the apparatus and method of the present invention may also be applied to prevent leakages of other fluids from body lumens in the same manner as described for the treatment of internal bleeding.

The exemplary embodiments of the present invention described herein relate to devices and methods for treating internal bleeding and, in particular, relate to methods and devices for treating GI tract bleeding. According to the present invention, a hemostatic device for treating internal bleeding is delivered to a target location via an endoscope, or other device adapted for less invasive surgical procedures. The hemostatic device is introduced, for example, via a natural body opening or a small incision and is placed over a target blood vessel to constrict the vessel and prevent the passage of blood therethrough.

An example of a minimally invasive hemostasis product available today is the Super 7© Multiple Band Ligation System, produced by Boston Scientific Corporation. This device has a cylindrical shell adapted to fit over the distal end of an endoscope, and a plurality of elastic bands stretched over the shell. When the endoscope reaches the desired location, the distal tip is maneuvered so that the cylindrical shell is located over a varix to be treated. Those skilled in the art will understand that varices are abnormally dilated or swollen veins, arteries or lymph vessels that are presently bleeding or that may soon start bleeding. Once the cylindrical shell body has been properly positioned, a deployment mechanism is actuated to release one of the bands over the varix. When the band is successfully deployed, the local cessation of blood flow destroys the varix at the location over which the band is placed.

During this procedure, the band strangulates the tissue of the varix which sloughs off within a few days. While the band (or bands) is loaded on the shell, it is stretched to a relatively large diameter. Once the band is deployed, for example by pulling it off the cylinder via a wire or cable, the band snaps back to its original un-stretched diameter which is sufficiently small that it strangulates the targeted varix causing the desired hemostasis. The sudden contraction of the band during deployment may make accurate placement difficult and, after release from the shell, the band cannot be repositioned. This further complicates the procedure, and may require additional attempts to position a band correctly over the target varix.

Embodiments of the present invention employ one or more coils made of a shape memory material which constrict around target tissue to strangle targeted varices. The shape memory material coils may be deployed from a delivery cylinder disposed at the distal end of an endoscope, to take advantage of the maneuverability and vision tools of the endoscope. The internal bleeding system and devices according to the invention provide hemostasis by means of a minimally invasive procedure, and can be used in hard to reach areas such as remote portions of the GI tract. Those skilled in the art will understand that shape memory materials are materials which, after plastic deformation, will return to an original shape (i.e., a shape of the material prior to plastic deformation) when a temperature of the material is elevated above a critical temperature.

Figure 1:
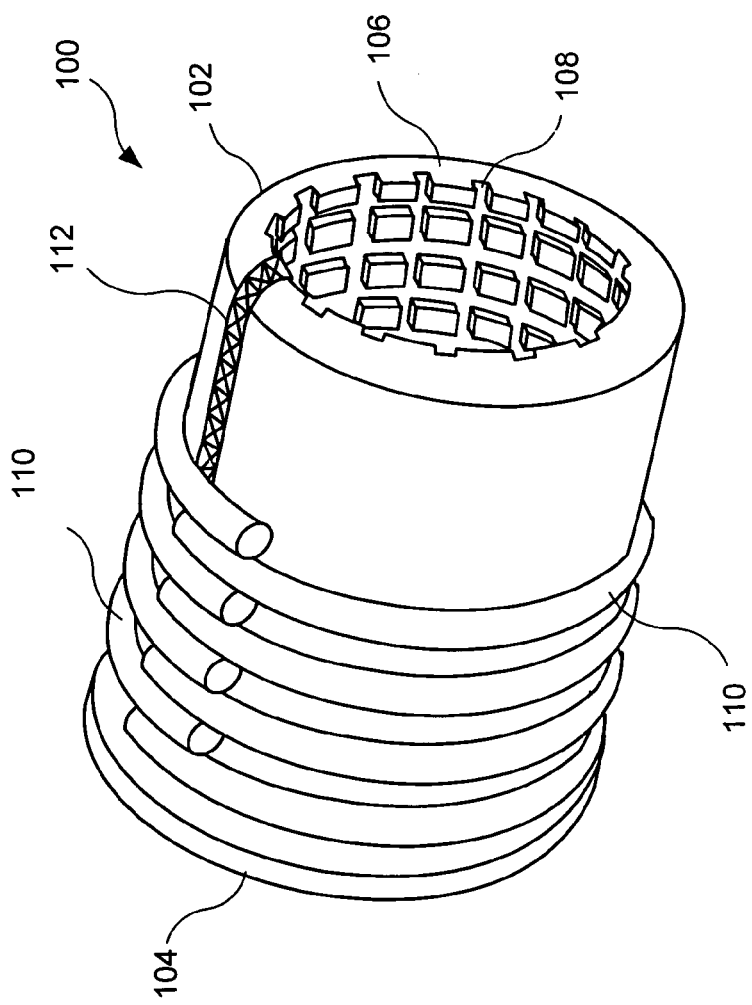
FIG. 1 is a perspective view showing an embodiment of a delivery cylinder for shape memory hemostasis bands according to the present invention.

An exemplary embodiment of a hemostasis band delivery device 100 according to the present invention is described with reference to FIG. 1. FIG. 1 shows a perspective view of a delivery cylinder 102 loaded with a plurality of shape memory hemostasis bands 110 according to the invention. The delivery cylinder 102, which is preferably designed to fit on the distal end of an endoscope, not shown here, has a shell-like construction and defines a longitudinal channel 108 with a diameter greater than the diameter of a distal end of the endoscope, extending from the proximal end 104 to the distal end 106 thereof. The delivery cylinder 102 slides over the distal end of the endoscope with the distal end 106 of the delivery cylinder 102 extending beyond the distal end of the endoscope. This facilitates positioning the delivery cylinder 102 in a desired position over a targeted varix, using the navigation and vision provided by the endoscope.

One or more shape memory hemostasis bands 110 are provided on the delivery cylinder 102. For example, the bands 110 may be carried on the outer surface of the delivery cylinder 102, as shown in FIG. 1. A plurality of bands 110 may be stacked longitudinally, such that they may be deployed sequentially from the delivery cylinder 102 over a plurality of varices. For example, a control cable 112 extending within the channel 108 may be used to pull the distal most one of the bands 110 toward the distal end of the delivery cylinder 102 to deploy the distal most band 110. After a band 110 has been successfully deployed, the endoscope and the delivery cylinder 102 may be repositioned over another varix and the subsequent distal-most band 110 may be deployed in the same manner as the previous band 110. A control rod may alternatively be used to push successive bands 110 past the distal end 106, away from the endoscope. As would be understood by those skilled in the art, any of the variety of conventional delivery and deployment mechanisms may be used in different embodiments to sequentially release the bands 110 from the delivery cylinder 102. Once the delivery cylinder 102 has been positioned over a target portion of tissue and the tissue has been drawn into the channel 108 (e.g., under suction or using graspers, etc.) and the band 110 has been released from the delivery cylinder 102 as described above, the tissue extends through a central opening 111 formed by the band 110. When positioned over the delivery cylinder 102, the bands 110 are in an expanded diameter, tissue-receiving configuration. After release therefrom, the temperature of the bands 110 increases from ambient temperature to body temperature and the bands 110 shrink to the reduced diameter tissue strangulating configuration.

Figure 3:
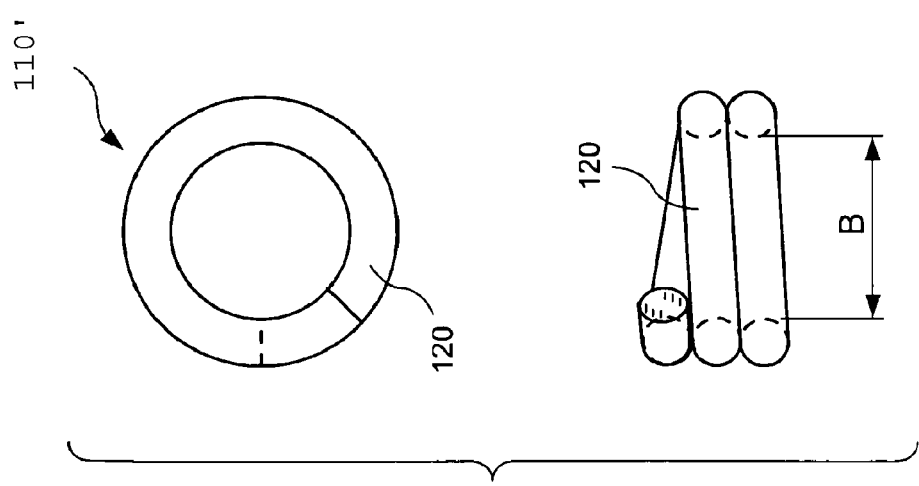
FIG. 3 is a diagram showing the hemostasis band of FIG. 2 in a contracted condition.

FIGS. 2 and 3, respectively, show a side elevation and a top plan view of an exemplary shape memory hemostasis band 110 according to the present invention. The hemostasis band 110 of FIG. 2 is in the tissue-receiving configuration (e.g., for loading onto the delivery cylinder 102). The hemostasis band 110' shown in FIG. 3 is in the tissue strangulating configuration (e.g., after deployment from the delivery cylinder 102). For example, the hemostasis band 110, 110' may be constructed from a wire 120 made from a shape memory material, coiled and shaped to form a substantially annular shell. The wire 120 may be treated during manufacture to give it a memorized shape to which, under predetermined conditions, the wire 120 will return after it has been mechanically deformed.

As shown in FIG. 3, in one exemplary embodiment, the wire 120 is manufactured with a memorized shape having a small operative diameter B, corresponding to the tissue strangulating configuration. Those skilled in the art will understand that any conventional methods may be used to obtain the desired memorized shape. The operative diameter B is selected such that it is sufficiently small to strangulate target varices after being deployed. Those skilled in the art will further understand that various bands 110 may be fabricated with a range of diameters B suitable for varices of a corresponding range of sizes. After manufacture, the hemostasis band is expanded to the larger tissue receiving diameter as shown in FIG. 2, for example, by applying a mechanical force to stretch the wire 120. As described above, the larger, tissue receiving diameter is selected to facilitate mounting of the band 110 onto the delivery cylinder 102 and an inner diameter of the channel 108 is selected to be large enough to accommodate the target varices. A radially outward force exerted against the bands 110 by the outer surface of delivery cylinder 102 retains the bands 110 in the expanded configuration. As described above, the vision system of the endoscope is used to guide the delivery cylinder 102 to a desired location over a target varix. Then, the varix is drawn into the channel 108 and the distal most shape memory band 110 is deployed over the target varix at which time it contracts tightly around the varix to the tissue strangulating configuration of diameter B. Those skilled in the art will understand that this system may be used to treat varices in any areas accessible by the endoscope including, for example, remote areas of the GI tract and may be used to treat other areas through surgical openings much smaller in size than required for open surgery to stop internal bleeding at those locations.

The shape memory properties of the material forming the coil wire 120 are preferably selected to achieve desired performance characteristics. For example, the transition from the diameter A to the diameter B may be initiated as a temperature of the bands 110 passes across a critical temperature threshold. Specifically, those skilled in the art will understand that a critical temperature of the bands 110 may be selected to be at or slightly below body temperature so that a phase change of the shape memory material will occur as the bands are warmed by ambient temperatures within the body past the critical temperature. Thus, in a first state, the shape memory band 110 may retain the diameter A while, after being heated by the body to a temperature higher than the critical temperature, the shape memory material transitions to a second state in which the bands 110 will, when in an unstressed state, resume the memorized shape with the smaller diameter B. Those skilled in the art will further understand that the properties of the shape memory material forming the bands 110 may be selected so that the transition is rapid or slow, depending on the needs of the medical procedure. Those skilled in the art will also understand that any of a variety of biocompatible shape memory materials, such as Nitinol and shape memory polymers, may be used to construct the bands 110.

In a different embodiment according to the invention, other mechanisms may be employed to initiate the transition of the hemostatic shape memory band from the larger tissue receiving configuration to the smaller tissue strangulation configuration. For example, external heating may be used to elevate the temperature of the shape memory material of the bands 110 or selected ones of the bands 110 over the critical temperature. Those skilled in the art will understand that this may be effected by exposing the bands 110 to microwaves, or magnetic and/or electric fields or radiated heat lasers. As described above, the material may simply return to the memorized operative diameter condition once the constraint posed by the delivery cylinder's outer surface is removed. In addition, a coating may be applied to the bands 110 prior to use. For example, an antibacterial coating, coatings that promote coagulation, or coatings having other therapeutic functions may be used. Lubricating coatings or coatings that modify the mechanical properties of the band also may be applied. Furthermore, the surface of any of the bands according to the invention may be modified to alter the resistance of the bands to popping off of a varix. For example, as would be understood by those skilled in the art, an inner diameter of a band may be corrugated or otherwise roughened to increase a gripping or frictional force between the band and the tissue.

Figure 4:
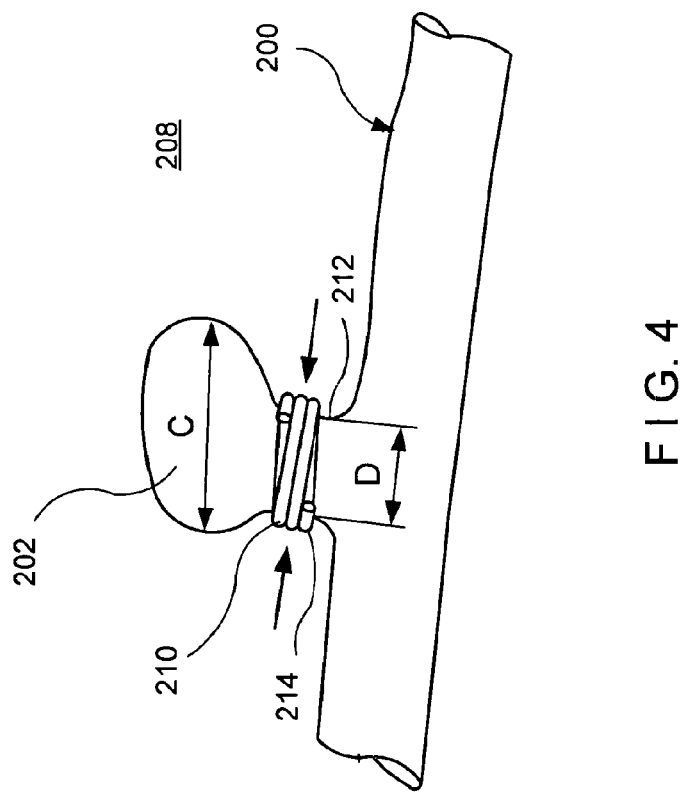
FIG. 4 is a diagram showing the hemostasis band of FIG. 3 deployed over a varix.

FIG. 4 shows an exemplary embodiment of a band 110 according to the invention, after transition to the tissue strangulation configuration over a varix in a wall of the GI tract 208 fed by a vessel 200 which is any of a vein, an artery or a lymph vessel. Although the invention is described in conjunction with the treatment of a varix in the GI tract 208, those skilled in the art will understand methods and devices according to the present invention are suitable for use in other parts of the body which may be difficult to reach.

As described above, a hemostasis band delivery device 100 is attached to the distal end of a delivery device such as an endoscope, colonoscope, laparoscope, etc. For example, the delivery cylinder 102 shown in FIG. 1 may be slipped over the outer circumference of a distal portion of the endoscope with one or more shape memory hemostasis bands (e.g., bands 210) mounted over the outer surfaces thereof. The bands 210 remain in place (via friction coupling to the delivery cylinder 102) until the user deploys them over the distal end of the delivery cylinder 102 around the target varix. The combination of endoscope and delivery cylinder 102 are inserted into the body, for example, through a naturally occurring body orifice to a hollow organ. The endoscope is then navigated to the target varix 202 using conventional methods and the delivery cylinder 102 is placed over the target varix 202 (e.g., under visual control). The user then draws a portion of tissue surrounding the target varix into the channel 108 in the delivery cylinder 102 using conventional methods such as graspers and/or suction. When a portion of tissue sufficient to ensure proper placement of the band 210 has been drawn into the channel 108, the user deploys the distal-most band 210 over the varix 202, preferably so that it resides near a base portion 212 of the varix 202. As described above, upon release of the band 210 from the delivery cylinder 102, the band contracts to the diameter B and strangulates the varix.

The shape memory hemostasis band 210 according to the invention may, for example, be formed as a coil of wire 214 formed, for example, of Nitinol or other suitable material. As described above, the inner diameter of the channel 108 is selected to be slightly larger than a dimension C of the target varices with the stretched diameter of the bands 210 being slightly larger than the inner diameter of the channel 108 (i.e., at least as large as an outer diameter of the delivery cylinder 102). This ensures that enough of the tissue adjacent to the varix will fit within the channel 108 and, consequently, ensures that the band 210 will be sufficiently large to easily pass over the protruding portion of the varix (diameter C portion) for mounting adjacent to a base thereof. The diameter B toward which the band 210 is biased to return is preferably less than a diameter D of the varix in an unstressed state so that strangulation is achieved.

Alternatively, any of the shape memory hemostasis bands according to the invention may be formed of a shape memory polymer. Polymeric shape memory materials have properties similar to those of the metallic shape memory alloys, although those properties result from different physical effects and processes. As such, elements formed from shape memory polymers may be given a base shape and then cooled below the critical temperature where a strain is applied to deform the polymer. When the element is heated again to a temperature above the critical temperature, it regains the shape that it had before the strain was applied. Examples of polymers that have been utilized in hard and soft phases of shape memory polymers include polyurethanes, polynorborenes, polyethers, polyacrylates, polyamides, polysiloxanes, polyether amides, polyether esters, trans-polyisoprenes, polymethylmethacylates, cross-linked trans-polyoctylenes, cross-linked polyethylenes, cross-linked polyisoprenes, cross-linked polycyclooctenes, inorganic-organic hybrid polymers, co-polymer blends with polyethylene and Kraton, styrene-butadiene co-polymers, urethane-butadiene co-polymers, PMMA, polycaprolactone or oligo caprolactone co-polymers, PLLA or PL/D LA co-polymers, PLLA PGA co-polymers, and photocrosslinkable polymers including azo-dyes, zwitterionic, and other photochromatic materials such as those described in "Shape Memory Materials" by Otsuka and Wayman, Cambridge University Press 1998, the entire contents of which are incorporated herein by reference.

The present invention has been described with reference to specific exemplary embodiments. Those skilled in the art will understand that changes may be made in details, particularly in matters of shape, size, material and arrangement of parts without departing from the teaching of the invention. Internal bleeding in different hollow organs may be treated by using the present invention, in addition to the GI tract. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. A system for treating internal bleeding in a patient, comprising:

a delivery cylinder having a longitudinal channel, an outer surface, a proximal end and a distal end, said proximal end being releasably connectable to a distal end of an endoscope and said distal end having a tissue-receiving opening adapted to receive tissue within the longitudinal channel; and a tissue-constricting element carried on the outer surface of the delivery cylinder, said tissue-constricting element comprising a solid wire in the shape of a coil with a central opening, the tissue-constricting element being formed of a shape memory material having a memorized shape, said tissue-constricting element having a first tissue-receiving configuration and a second tissue-constricting configuration, wherein said second tissue-constricting configuration is the memorized shape, and wherein in the first tissue-receiving configuration, the central opening of the coil has a first expanded diameter and in the second tissue-constricting configuration, the central opening of the coil has a second contracted diameter that is smaller than the first expanded diameter.

2. The system according to claim 1, wherein the tissue-constricting element comprises a coating including one of a coagulation promoting agent and an antibacterial agent.

3. The system according to claim 1, further comprising an actuator element coupled to the tissue-constricting element for deploying the tissue-constricting element from the delivery cylinder.

4. The system according to claim 1, wherein the tissue-constricting element is formed of Nitinol.

5. The system according to claim 1, further comprising a plurality of tissue-constricting elements carried on the delivery cylinder.

6. The system according to claim 1, wherein, when carried on the delivery cylinder, the tissue-constricting member is in the first tissue-receiving configuration.

7. The system according to claim 1, wherein a critical temperature of the shape memory material is selected so that, as the tissue-constricting element is warmed by body heat, a phase change in the shape memory material urges the tissue-constricting element toward the memorized shape.

8. The system according to claim 1, wherein the shape memory material includes a shape memory polymer.

9. The system according to claim 8, wherein the shape memory polymer includes one of polyurethane, polynorborene, polyether, polyacrylate, polyamide, polysiloxane, polyether amide, polyether ester, trans-polyisoprene, polymethylmethacylate, cross-linked trans-polyoctylene, cross-linked polyethylene, cross-linked polyisoprene, cross-linked polycyclooctene, an inorganic-organic hybrid polymer, a co-polymer blend with polyethylene and Kraton, a styrene-butadiene co-polymer, an urethane-butadiene co-polymer, PMMA, polycaprolactone co-polymer, oligo caprolactone co-polymer, PLLA co-polymer, PL/D LA co-polymer, PLLA PGA co-polymer, and a photocrosslinkable polymer including one of an azo-dye, and zwitterionic.

10. The system according to claim 1, wherein the tissue-constricting element is of a size capable for deployment inside a body lumen.

11. The system of claim 1, wherein a tissue-contacting surface of the tissue-constricting element is corrugated to enhance a tissue-gripping capacity.

12. The system of claim 1, wherein, when the tissue constricting element transitions from the tissue-receiving configuration to the tissue-constricting configuration, a number of loops of the coil increases by at least one.

13. A method for treating of fluid leakage within a living body, comprising:
using a delivery cylinder having a longitudinal channel, an outer surface, a proximal end and a distal end, said proximal end being releasably connectable to a distal end of an endoscope and said distal end having a tissue-receiving opening adapted to receive tissue within the longitudinal channel, said delivery cylinder having a plurality of tissue-constricting elements on the outer surface thereof, each tissue-constricting element comprising a solid wire in the shape of a coil with a central opening, each tissue-constricting element being formed of a shape memory material having a memorized shape, each tissue-constricting element having a first tissue-receiving configuration and a second tissue-constricting configuration, wherein said second tissue-constricting configuration is the memorized shape, and wherein in the first tissue-receiving configuration, the central opening of the coil has a first expanded diameter and in the second tissue-constricting configuration, the central opening of the coil has a second contracted diameter that is smaller than the first expanded diameter;
inserting the delivery cylinder with the plurality of tissue-constricting elements thereon into the body;
drawing a first portion of tissue into the tissue-entry opening while maintaining a first tissue-constricting element of the plurality of tissue-constricting elements in the tissue-receiving configuration; and
changing the first tissue-constricting element to the tissue-constricting configuration to strangulate the first portion of tissue.

14. The method according to claim 13, further comprising applying electromagnetic energy to the tissue-constricting elements to cause a phase change of the shape memory material.

15. The method according to claim 13, after changing the first tissue-constricting element to the tissue-constricting configuration, drawing a second portion of tissue into the tissue-entry opening of a second tissue-constricting element of the plurality of tissue-constricting elements while maintaining the second tissue-constricting element in the tissue-receiving configuration; and
changing the second tissue-constricting element to the tissue-constricting configuration to strangulate the second portion of tissue.

16. The method according to claim 13, further comprising attaching the delivery cylinder to a distal end of an endoscope.

17. The method according to claim 13, wherein the shape memory material includes a shape memory polymer.

18. The method according to claim 17, wherein the shape memory polymer includes one of polyurethane, polynorborene, polyether, polyacrylate, polyamide, polysiloxane, polyether amide, polyether ester, trans-polyisoprene, polymethylmethacylate, cross-linked trans-polyoctylene, cross-linked polyethylene, cross-linked polyisoprene, cross-linked polycyclooctene, an inorganic-organic hybrid polymer, a co-polymer blend with polyethylene and Kraton, a styrene-butadiene co-polymer, an urethane-butadiene co-polymer, PMMA, polycaprolactone co-polymer, oligo caprolactone co-polymer, PLLA co-polymer, PLD LA co-polymer, PLLA PGA co-polymer, and a photocrosslinkable polymer including one of an azo-dye, and zwitterionic.

19. The method according to claim 13, wherein the first tissue-constricting element is of a size capable for deployment inside a body lumen.

20. The method of claim 13, wherein a tissue-contacting surface of the tissue-constricting element is corrugated to enhance a tissue-gripping capacity.

21. The method of claim 13, wherein, when the tissue constricting element transitions from the tissue-receiving configuration to the tissue-constricting configuration, a number of loops of the coil increases by at least one.

* * * * *